United States Patent [19]

Whittaker et al.

[11] 4,337,262
[45] Jun. 29, 1982

[54] HYDANTOIN DERIVATIVES, PHARMACEUTICAL COMPOUNDS AND METHODS OF USE

[75] Inventors: Norman Whittaker, Beckenham; Albert G. Caldwell, West Wickham, both of England

[73] Assignee: Burroughs Wellcome Co., Research Triangle Park, N.C.

[21] Appl. No.: 964,928

[22] Filed: Nov. 30, 1978

[30] Foreign Application Priority Data

Dec. 1, 1977 [GB] United Kingdom ............... 50090/77

[51] Int. Cl.³ .................. C07D 233/78; A61K 31/415
[52] U.S. Cl. ................................ 424/273 R; 548/312; 548/313; 260/464; 260/465.4; 560/115; 560/169; 562/507; 562/564
[58] Field of Search ........................ 548/308, 312, 313; 424/273 R

[56] References Cited

U.S. PATENT DOCUMENTS

| | | | |
|---|---|---|---|
| 2,833,780 | 5/1958 | Schmitz | 548/313 |
| 3,197,477 | 7/1965 | Gubitz et al. | 548/308 |
| 3,256,247 | 6/1966 | Gagliardi et al. | 548/313 |
| 3,576,858 | 4/1971 | Mizuguchi et al. | 548/313 |
| 4,057,571 | 11/1977 | Grudzinskas et al. | 560/121 |
| 4,147,796 | 4/1979 | Wootton | 548/313 |
| 4,152,445 | 5/1979 | Wootton | 548/312 |

FOREIGN PATENT DOCUMENTS

| | | |
|---|---|---|
| 2362839 | 3/1978 | France . |
| 2374309 | 7/1978 | France . |
| 45/31959 | 10/1970 | Japan ................................. 548/313 |
| 1346279 | 2/1974 | United Kingdom . |
| 1529275 | 10/1978 | United Kingdom . |

OTHER PUBLICATIONS

Smith et al., Jour. of Med. Chem. 1977, vol. 20, No. 10, pp. 1292–1299.

*Primary Examiner*—Jane T. Fan
*Attorney, Agent, or Firm*—Donald Brown

[57] ABSTRACT

Hydantoins of formula (I)

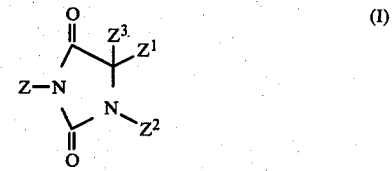

have biological properties related to those of naturally occurring prostaglandins and may be used in medicine, for example in the treatment of thrombosis.

31 Claims, No Drawings

HYDANTOIN DERIVATIVES, PHARMACEUTICAL COMPOUNDS AND METHODS OF USE

This invention relates to heterocyclic compounds, their synthesis, intermediates therein, compositions containing the heterocyclic compounds and their use in medicine.

Hydantoin, derivatives, defined hereinbelow in formula (I), have been found by the applicants to have pharmacological properties related to those of natural prostaglandins, as demonstrated by their ability to mimic or antagonise the physiological effects of the natural prostaglandins in various biological preparations. In particular, certain compounds of formula (I) have been found to be potent mimetics of the anti-platelet aggregatory properties of prostaglandin $E_1$.

In formula (I)

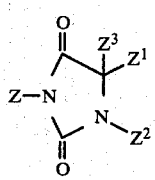

Z is hydrogen or alkyl;
one of $Z^1$ and $Z^2$ is represented by the group —$CH_2$—X—$X^1$—$X^2$ wherein X is phenylene, —C≡C—, cis or trans —CH=CH— or —$CH_2$—$CQ_2$—
in which each Q is independently selected from hydrogen and alkyl, such as ethyl, or the Q's together form an alkylene radical having four, five or six carbon atoms; $X^1$ is a covalent bond or a straight or branched alkylene chain having from 1 to 6 carbon atoms optionally having one of any methylene groups replaced by oxa (—O—) or thia(—S—) provided that at least one carbon atom separates such an oxa or thia group from a —C≡C—, —CH=CH— or —CO— group; and $X^2$ is selected from 5-tetrazolyl, carboxyl, carboxamide, hydroxymethylene and alkoxycarbonyl;
and the other of $Z^1$ and $Z^2$ is represented by the group —Y—$Y^1$—$Y^2$—$Y^3$
wherein Y is —$CR_2CH_2$— in which each R is independently selected from hydrogen and methyl; $Y^1$ is carbonyl, methylene, methylene substituted by hydroxyl or methylene substituted by hydroxyl and alkyl; $Y^2$ is a covalent bond or straight or branched alkylene having from 1 to 7 carbon atoms optionally substituted on the carbon adjacent $Y^1$ by one or two groups each of which may be alkyl or a cyclic radical, $Y^3$ is hydrogen, hydroxy, alkoxy having from 1 to 7, preferably 1 to 4, carbon atoms, a cyclic radical, phenyl, benzyl, phenoxy or benzyloxy, wherein each of phenyl, benzyl, phenoxy and benzyloxy may be substituted in the benzene ring by one or more groups selected from hydroxy, halogeno, nitro, amino, acylamino, alkenyl, alkoxy, phenyl and alkyl which may itself be substituted by one or more halogeno groups; or $Y^2$ and $Y^3$ together form an alkyl group having 1 to 7 carbon atoms at least one hydrogen of which is replaced by fluoro; or Y is a bond, —$CH_2$— or —$CH_2.CH_2$— and $Y^1$, $Y^2$ and $Y^3$ taken together form a cycloalkyl or bicycloalkyl group substituted by a hydroxyl group which preferably has three carbon atoms separating it from the hydantoin ring; and $Z^3$ is —$CH_2$—X—$X^1$—$X^2$ as defined above, preferably ω-carboxylalkyl, or alkyl having from 1 to 8 carbon atoms, preferably 1 to 6 carbon atoms, preferably methyl.

In formula (I), the term cyclic radical in the definitions of $Y^2$ and $Y^3$ means the monovalent radical derived by loss of a ring hydrogen atom from a monocyclic or polycyclic compound excluding benzene, (i.e. excluding phenyl) having from 3 to 12 ring atoms selected from carbon, nitrogen, oxygen and sulphur, which compound may be saturated or unsaturated and may be further substituted by one or more alkyl, fluoro or fluorine-substituted alkyl groups. Such cyclic radicals include cycloalkyl having from 3 to 10 carbon atoms such as cyclopropyl, cyclopentyl, cyclohexyl and cyclooctyl, bicycloalkyl having from 4 to 10 carbon atoms such as adamantyl or norbornanyl (bicyclo[2,2,1-]heptyl), spiroalkanyl having from 5 to 12 carbon atoms such as 2-spiro[3,3]heptyl, 1-spiro[4,4]nonane and 8-spiro[4,5]decane, cycloalkenyl having from 4 to 10 carbon atoms such as 4-cyclopentyl, heterocyclic radicals such as tetrahydrofuranyl and tetrahydropyranyl and heteroaryl radicals such as thienyl, furyl, pyridyl, pyrimidyl, thiazolyl, imidazolyl and diazepinyl. As indicated above included in the term cyclic radical are these wherein one or more hydrogen atoms are replaced by fluoro.

Unless otherwise stated, in formula (I) and other formulae in this specification, alkyl moieties are selected from methyl, ethyl, propyl, butyl, pentyl and hexyl, including all isomers thereof, i.e. having from 1 to 6 carbon atoms; for example, in the definitions of $Y^1$ and $Y^2$ the alkyl groups are preferably methyl; and the alkyl moiety of alkoxycarbonyl is desirably methyl or ethyl. Similarly alkylene groups have from 2 to 4 carbon atoms, for example vinyl.

In a compound of formula (I) the bonding of the divalent phenylene group may be ortho, meta, or para and the oxa or thia group is preferably adjacent the phenylene or when X is other than phenylene then $X^1$ may be —$CH_2$—O—$CH_2$— or $CH_2$—S—$CH_2$.

Included in the meaning of compounds of formula (I) are bioprecursers thereof and the salts corresponding to the carboxylic acids and tetrazoles when $X^2$ is carboxyl or tetrazolyl respectively, and the salts which may also be formed when Z is hydrogen. Particularly valuable salts for medical purposes are those having a pharmaceutically acceptable cation, such as ammonium or that of an alkali metal e.g. sodium and potassium, an alkaline earth metal e.g. calcium and magnesium, or an organic base, particularly an amine, such as ethanolamine. Salts having non-pharmaceutically acceptable cations are included within the ambit of this invention as useful intermediates to pharmaceutically acceptable salts, or the acids or esters of formula (I).

Except when there is clear indication to the contrary, formula (I) and other formulae in the specification embrace all stereoisomers represented therein. In particular such formulae include the enantiomeric forms, such mixtures as are designated racemates, and diastereoisomers.

The compounds having particularly interesting prostaglandin-related properties are those of formula (I) wherein Z is hydrogen or alkyl having from 1 to 4 carbon atoms;
one of $Z^1$ and $Z^2$ is —$CH_2$—X—$X^1$—$X^2$ wherein X and $X^1$ taken together form alkylene of from 3 to 7, in particular 5, carbon atoms, and $X^2$ is alkoxycarbonyl, carboxyl or a salt thereof;

and the other of $Z^1$ and $Z^2$ is $-Y-Y^1-Y^2-Y^3$ wherein Y, $Y^1$ and $Y^2$ are as hereinbefore defined and $Y^3$ is hydrogen, or cycloalkyl of from 4 to 7 carbon atoms. Within this definition are included the subclass wherein Z is hydrogen and $Z^1$ is $-CH_2-X-X^1-X^2$ as defined.

The most preferred compound is 5-(6-carboxyhexyl)-1-(3-cyclohexyl-3-hydroxypropyl)-5-methyl-hydantoin, less polar isomer, or a salt or ester thereof.

The compounds of formula (I) may be synthesised by any method known in the art for the synthesis of compounds of analogous structure. For example, they may be prepared from the corresponding derivatives of hydantoic acid of formula (II)

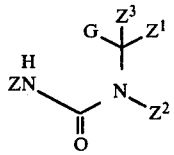   (II)

wherein G is carboxyl or a derivative thereof such as amide or ester in particular an alkyl ester, and each of $Z, Z^1$, $Z^2$ and $Z^3$ has the same meaning as in formula (I), by cyclisation under acidic conditions or by heating alone. The reactions may be effected in the absence of a solvent, but if desired an inert solvent may be used, for example a hydrocarbon such as petrol. Alternatively, where G is alkoxycarbonyl cyclisation may be effected in the presence of a suitable base, for example an alkoxide such as sodium ethoxide.

Compounds of formula (II) are conveniently prepared from an amino acid derivative of formula (III)

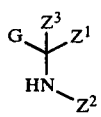   (III)

wherein $G, Z^1$, $Z^2$ and $Z^3$ are as defined in formula (I) provided that G may also be nitrile, by reaction with cyanic acid or an alkyl iso-cyanate depending respectively on whether Z is hydrogen or alkyl.

When cyanic acid is used, the cyanic acid is conveniently produced in situ by the use of an alkali metal cyanate, e.g. potassium cyanate, and an acid which may be present as an acid addition salt of the compound of formula (III) or a free acid of formula (III) wherein either or both of R and $X^2$ is hydrogen. Alternatively an equivalent amount of mineral acid or an organic acid may be added to the reaction medium. The reaction may proceed in the absence of a solvent, but desirably an inert solvent is used which is preferably polar such as water or a mixture of water with acetone, dimethylformamide, dimethylsulphoxide or a lower alkanol such as ethanol or it may be a hydrocarbon, an ether or halogenated hydrocarbon such as chloroform. Where desired, for example if no solvent is used, the reaction may be promoted by heating the reactants.

Similar reaction conditions may be used when an alkyl isocyanate is used except that it is unnecessary to provide an equivalent amount of acid, as an acid addition salt or otherwise, in the reactants.

Instead of using a cyanate or isocyanate, a compound of formula (III) may be reacted with urea, nitrourea or an N-alkylurea as appropriate. A solvent is not essential but if desired an inert solvent such as one mentioned above may be used, and the reaction is preferably effected at an elevated temperature, for example from 100° to 125° C. but temperatures up to 150° C. may be employed.

In the above described synthesis, the intermediates of formula (II) need not be isolated from the reaction mixture and may be converted directly to compounds of formula (I) under the described reaction conditions.

An intermediate of formula (III) may be conveniently prepared by reaction of a compound of formula (IV) with a compound of formula (V)

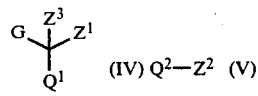   (IV) $Q^2-Z^2$   (V)

wherein G, $Z^1, Z^2$ and $Z^3$ are as defined in formula (III), one of $Q^1$ and $Q^2$ is amino and the other is halogeno, preferably bromo. The reaction may be carried out by heating in the absence of solvent or in the presence of an inert solvent such as ethanol.

The intermediates of formula (III) wherein $Z^2$ is $-Y-Y^1-Y^2-Y^3$ when $Y^1$ is carbonyl may also be prepared by reaction of an amine of formula (IV) wherein $Q^1$ is amino with an unsaturated ketone of formula (VI)

$$CR_2=CH.CO.Y^2.Y^3 \qquad (VI)$$

wherein $Y^2$ and $Y^3$ have the same meaning as in formula (III); the reaction being effected in the presence or absence of an inert solvent, and at room temperature or optionally with heating.

The intermediates of formula (IV) may themselves be prepared by alkylation of a corresponding compound of formula (IV A)

   (IV A)

wherein G, $Q^1$ and $Z^1$ have the same meaning as in formula (IV). The reaction is preferably carried out by reacting the appropriate alkylating agent, such as an alkyl halide, with a corresponding Schiff's base under basic conditions, for example in the presence of sodium hydride; after alkylation the desired amine of formula (IV) is obtained by hydrolysis of the Schiff's base under acidic conditions.

Hydantoins of formula (I) may also be prepared by cyclisation of a compound of formula (VII)

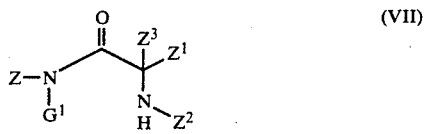   (VII)

wherein Z, $Z^1, Z^2$ and $Z^3$ are as defined in formula (I) and $G^1$ is carboxyl or a reactive derivative thereof such as alkoxycarbonyl e.g. ethoxycarbonyl. Compounds of formula (VII) may be cyclised under similar conditions as a compound of formula (II) and conveniently the method used to prepare a compound of formula (VII) is chosen such that the prevailing reaction conditions permit spontaneous cyclisation.

For example, the intermediates of formula (VII) may be prepared by reacting a compound of formula (V) with a compound of formula (VIII)

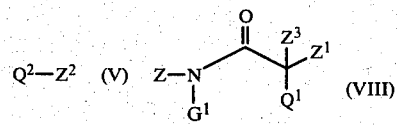

wherein one of $Q^1$ and $Q^2$ is halogeno, preferably chloro or bromo and the other is amino and each of $Z,Z^1,Z^2,Z^3$ and $G^1$ have the same meaning as in formula (VII). The reaction may be effected by admixture of the reactants or optionally an inert solvent is used and the mixture is heated. Suitable solvents include alkanols, ethers, hydrocarbons and halogenated hydrocarbons.

The compounds of formula (VIII) may themselves be made by reacting an appropriate carbamic acid derivative, for example an alkyl ester, with a compound of formula (IV), using techniques known to those skilled in the art.

In a method related to those described hereinbefore, the hydantoins of formula (I) may be prepared by reacting a compound of formula (IX)

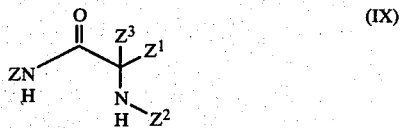

wherein each of $Z,Z^1,Z^2$ and $Z^3$ has the same meaning as in formula (I) with a carbonic acid derivative. Any carbonic acid derivative known to those skilled in the art as appropriate may be used, for example phosgene, diphenylcarbonate or an alkyl haloformate such as ethyl chloroformate. The reaction is desirably effected in the presence of a base, for example an amine such as triethylamine or di-iso propyl ethylamine, and using an inert aprotic solvent such as toluene, dimethylformamide or an ether such as diethylether. The reaction may be carried out at room temperature but if desired the reaction mixture may be heated.

The intermediates of formula (IX) may be made using methods analogous to those described above for the preparation of compounds of formula (III).

The hydantoins of formula (I) wherein Z is alkyl may also be prepared by alkylation, using an alkylating agent which may be designated as a reactive ester derivative of an alcohol $J^4.OH$, of a compound of formula (X)

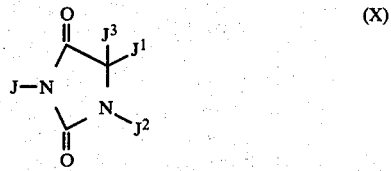

wherein $J^4$ has the same meaning as $Z^1$ or $Z^2$, each of J and $J^3$ has the same meaning as Z and $Z^3$ repectively, one of $J^1$ and $J^2$ is hydrogen and the other is $Z^1$ when $J^4$ is $Z^2$ or vice versa; or $J^4$ is alkyl, $J^1$ and $J^2$ have the same meaning as $Z^1$ and $Z^2$ respectively, one of J and $J^3$ is hydrogen and the other is hydrogen or alkyl.

Suitable reactive ester derivatives include chloride, bromide, iodide and sulphonates such as p-toluenesulphonate, methanesulphonate and benzenesulphonate.

The alkylation may be effected using reaction conditions which are known in the art to be suitable, for example in the presence of a base such as an alkali metal hydride, alkali metal amide or alkali metal alkoxide, typically sodium hydride or a sodium alkoxide e.g. sodium methoxide.

The reaction is conveniently carried out in an inert solvent which simply acts as a diluent for the reactants such as toluene, dioxan, ether, dimethylformamide, tetrahydrofuran, dimethylsulphoxide or acetonitrile or when the base is an alkali metal alkoxide then the corresponding alkanol may be used.

It will be appreciated that the intermediates of formula (X) wherein J is hydrogen are also compounds of formula (I) and may be prepared by one of the foregoing methods. The compounds of formula (X) may further be prepared by adaptation of methods already known in the art (see for example Chemical Reviews (1950) 46, p. 403–425).

Tetrazoles of formula (I) ($X^2$ being 5-tetrazolyl) may be prepared from corresponding compounds wherein the group $-X^2$ is replaced by

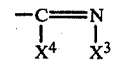

wherein $X^3$ and $X^4$ together form a bond (nitrile), $X^3$ is hydrogen or alkyl and $X^4$ is alkoxy (imidoester), alkylthio (imidothioester), $-NH-NH_2$ (amidrazone), or amino (amidine) or $R^3$ is hydroxy and $R^4$ is amino (amidoxime). The reaction is preferably carried out in a polar aprotic liquid medium such as dimethylformamide using a salt of a hydrazoic acid eg. sodium azide. However, when $X^2$ is replaced by an amidine or amidrazone, a suitable reagent is nitrous acid. If an amidine is reacted with nitrous acid then reduction of the intermediate nitrosation product, with or without prior isolation, using for example sodium amalgam, is required to give the corresponding tetrazole. The precursor to the tetrazole may be obtained by well known methods, for example the nitrile may be obtained by dehydration of the corresponding amide.

The alcohols of formula (I) wherein $X^2$ is hydroxymethylene may also be obtained by reduction with an appropriate reducing agent of the corresponding acid, ester, acid halide, acid anhydride or aldehyde. The appropriate reducing agent will depend on the particular substrate, but a reagent which may be used is sodium in ethanol.

A carboxylic acid may for example be converted to a corresponding mixed anhydride with ethyl chloroformate in the presence of a base such as triethylamine, and subsequently reduced to the alcohol using sodium borohydride. Similarly an ester may be reduced to the alcohol using di-iso-butyl aluminium hydride in an inert solvent such as ether or hydrocarbon such as hexane or benzene. Such alcohols may also be prepared by catalytic hydrogenation.

Alternatively hydroxyl group containing compounds of formula (I) especially the alcohols wherein $X^2$ is hydroxymethylene, may be prepared by hydrolysis of a corresponding halide with an appropriate reagent. For this purpose a hydroxide may be used, for example an aqueous alkali or a suspension of silver oxide in water.

In the synthesis of hydantoins of formula (I) having a hydroxyl group in a side chain it may be desirable to protect this hydroxyl group during the course of the reaction. This may be readily effected in known manner using a protecting group such as acyl, aroyl, tetrahydropyran-2-yl, 1-ethoxyethyl or arylalkyl, for example benzyl.

Removal of protecting groups may be carried out by appropriate methods known to those skilled in the art: for example an acyl group may be removed by acid or base hydrolysis, and a benzyl group by reductive cleavage.

Furthermore a ketone of formula (I) wherein $Y^1$ is carbonyl may be converted to the corresponding secondary alcohol by reduction with a suitable reducing agent, such as sodium borohydride. Also, an alcohol of formula (I) wherein $Y^1$ is —CHOH may be oxidised to the corresponding ketone using Jones' reagent, acid dichromate or any other suitable reagent.

Similarly where the compounds of formula (I) have a C≡C or CH=CH (or —CH=CQ—) bond these may be converted by conventional hydrogenation techniques, for example using a Lindlar type or Adams catalyst, to the corresponding ethylenic or saturated compounds as appropriate.

The hydantoins of formula (I) have an asymmetric 5-carbon atom, and a further asymmetric centre is present in those compounds wherein $Y^1$ includes a hydroxyl group. Such alcohols therefore exist as four isomers which are separable by thin layer chromatography or high performance liquid chromatography into two diastereomers, (the less polar being preferred) each of which is a racemic mixture of two isomers. On separation of the diastereomers, one diastereomer may be converted to a mixture of the four isomers by treatment with a base, such as an alkali metal hydroxide, and subsequently reseparated to provide two diastereomers. Repeated use of this technique enables the conversion of one diastereomer to the other; this may be desirable when one diastereomer has a biological activity which is preferred to that of the other diastereomer. If $Z^1$ and $Z^3$ are exactly the same then optical activity is absent at the 5-carbon atom.

The corresponding alcohols of formula (III), (IV) or (IVA) also exist in four isomeric forms. If desired, these may be separated into two epimers and subsequent cyclisation to a compound of formula (I) retains the stereochemical configuration.

Other asymmetric centres can also be present, for example if only one Q in formula I is other than hydrogen.

In all of the foregoing chemical procedures it is of course evident that the choice of reactant will be dictated in part by the functional groups present in the substrate, and where necessary reactants having an appropriate selectivity of action must be used.

The hydantoins of formula (I) are of value in having pharmacological properties related to those of natural prostaglandins; that is, the hydantoins mimic or antagonise the biological effects of members of the prostaglandin (PG) 'A', 'B', 'C', 'D', 'E', and 'F' series. For example, hydantoins of formula (I) have been found to mimic the anti-aggregatory effect of PGE, on blood platelets, and to antagonise the contraction induced by $PGE_2$ or $PGF_2$ on smooth muscle taken from the rat stomach, rat colon, chick rectum and guinea pig trachea. In general, antagonistic properties, as opposed to mimetic, have been observed when using larger doses of the hydantoins. The pharmacological profile, by which is meant the relative activities, mimetic or antagonistic, compared with the natural prostaglandins, will of course vary depending on the specific hydantoin under consideration.

By reason of their prostaglandin-related properties, the hydantoins of formula (I) are useful in the pharmacological characterisation and differentiation of the biological activities of the natural prostaglandins and their 'receptors'. The further understanding of the physiological role of prostaglandins is of course valuable in the search for new and improved therapeutic substances.

The hydantoins of formula (I) are also therapeutic agents. For example, hydantoins such as those described hereinbefore as having a potent anti-aggregatory effect on blood platelets are useful when it is desired to inhibit platelet aggregation or to reduce the adhesive character of platelets, and may be used to treat or prevent thrombo-embolic disorders, e.g. the formation of thrombi, in mammals, including man. For example, the compounds are useful in the treatment and prevention of myocardial infarcts, to treat and prevent thrombosis, to promote patency of vascular grafts following surgery, and to treat complications of arteriosclerosis and conditions such as atherosclerosis, blood clotting defects due to lipaemia, and other clinical conditions in which the underlying aetiology is associated with lipid imbalance or hyperlipidemia. A further use for such compounds is as an additive to blood and other fluids which are used in artifical extracorporeal circulation and perfusion of isolated body portions.

A group of compounds which are particularly valuable as inhibitors of platelet aggregation are those of formula (I) wherein Z is hydrogen; $Z^1$ is carboxyalkylene wherein the alkylene moiety has from 3 to 9 carbon atoms; and $Z^2$ is a group —$(CH_2)_2CHOH.Y^2.Y^3$ wherein $Y^2$ is a bond or branched alkylene having a tertiary carbon atom adjacent the hydroxy-substituted carbon and $Y^3$ is as defined in formula (I). Within this group of compounds, those wherein $Z^1$ is ω-carboxyhexyl and $Y^3$ is cycloalkyl having from 4 to 7 carbon atoms are especially active, $Z^3$ preferably being methyl or ω-carboxyhexyl.

The hydantoins of formula (I) also cause relaxation of vascular smooth muscle in a similar way as do members of the prostaglandin 'A' and 'E' series. Compounds relaxing vascular smooth muscle are capable of inducing vasodilation and therefore have antihypertensive properties and are useful in lowering the blood pressure in mammals, including man, and may be used alone or in combination with a β-adrenoceptor blocking agent or another antihypertensive substance for the treatment of all grades of hypertension including essential, malignant and secondary hypertension.

The compounds of formula (I) also mimic the effect of $PGE_1$ of antagonising histamine-induced bronchoconstriction. Compounds (I) having this property may be used in the treatment or prophylaxis of bronchial asthma and bronchitis by alleviating the bronchoconstriction associated with this condition.

Hydantoins of formula (I), which inhibit pentagastrin-induced gastric acid secretion and reduce the formation of aspirin-induced gastric lesions in rats are useful in reducing excessive gastric acid secretion, reducing and avoiding gastro intestinal ulcer formation and accelerating the healing of such ulcers already present in the gastrointestinal tract whether such ulcers arise spontaneously or as a component of polyglandular adenoma syndromes.

Intravenous infusions of hydantoins of formula (I) to dogs increase the urine volume indicating a potential utility for such compounds as diuretic agents, the uses of which include the treatment of oedema, for example oedema associated with heart failure, liver failure or kidney failure in man or other mammals.

A further use for hydantoins of formula (I) which mimic the effects of $PGE_2$ and $PGF_{2\alpha}$ on uterine smooth muscle is as antifertility agents, in particular as abortifacients.

In addition the compounds of formula (I) may be used in the treatment of proliferative skin diseases such as are associated with excessive cell division in the epidermis or dermis which may be accompanied by incomplete cell differentiation. Particular conditions which may be alleviated include psoriasis, atopic dermatitis, nonspecific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domestic animals. For the treatment of these conditions the compounds are desirably applied topically to the affected skin. Alternatively they may be administered by an intradermal or intramuscular injection which may be directly into the skin lesion or into the surrounding tissue. Injectable compositions will generally contain from 0.1 to 0.5% w/v of active ingredient.

The amount of a compound of formula (I) required to achieve the desired biological effect will of course depend on a number of factors, for example, the specific compound chosen, the use for which it is intended, the mode of administration, and the recipient. In general, a daily dose lies in the range of from 1 $\mu$g to 20 mg per kilogram bodyweight, preferably the daily dose is 10 $\mu$g to 2 mg, especially 100 $\mu$g to 0.2 mg (200 $\mu$g), per kilogram bodyweight. For example, an intravenous dose may lie in the range of from 5 $\mu$g to 1 mg/kg preferably 50 $\mu$g to 100 $\mu$g/kg, which may conveniently be administered as an infusion of from 0.01 to 50 $\mu$g preferably 0.1 to 5 $\mu$g, especially 0.5 to 1.5 $\mu$g, per kilogram per minute. Infusion fluids suitable for this purpose may contain from 0.001 to 100, for example from 0.01 to 10 $\mu$g, per milliliter. Unit doses may contain from 10 $\mu$g to 100 mg of a compound of formula (I) depending on how the compound is to be administered, for example ampoules for injection may contain from 0.01 to 1 mg, preferably 0.05 to 0.15 mg, for example 0.1 mg, and orally administrable unit dose formulations such as tablets or capsules may contain from 0.1 to 50, preferably 2 to 20 mg, especially 5 to 15 mg, for example 10 mg.

More specifically, when a compound of formula (I) is used to inhibit platelet aggregation it is generally desirable to achieve a concentration in the appropriate liquid, whether it be the blood of a patient or a perfusion fluid, of about 1 $\mu$g to 10 mg, preferably from 10 $\mu$g to 1 mg, especially 0.05 to 0.15 mg, for example 0.1 mg, per liter.

The abovementioned doses refer to the acids, amides, esters, alcohols and tetrazoles of formula (I); where a salt is used, the dose should be taken as referring to the corresponding anion.

For use in the treatment or prophylaxis of the conditions referred to above, while the hydantoin compounds may be used as the raw chemical they are preferably presented with an acceptable carrier therefor as a pharmaceutical formulation. The carrier must be 'acceptable' in the sense of being compatible with the other ingredients of the formulation and not deleterious to the recipient thereof. The carrier may be a solid or a liquid, and is preferably formulated with a hydantoin compound as a unit-dose formulation, for example a tablet, which may contain from 0.05% to 95% by weight of the hydantoin compound. Other pharmacologically active substances may also be present in formulations of the present invention as indicated above. The hydantoin compounds may be incorporated in the formulations either in the form of the acid or the salt or ester (or amide) thereof, and the formulations may be prepared by any of the well-known techniques of pharmacy consisting essentially of admixture of the components of the formulation.

The formulations include those suitable for oral, rectal, topical, buccal (e.g. sub-lingual), parenteral (that is subcutaneous, intramuscular and intravenous) administration, although the most suitable route in any given case will depend on the nature and severity of the condition being treated, and on the hydantoin compound.

Formulations suitable for oral administration may be presented as discrete units, such as capsules, cachets, lozenges or tablets, each containing a predetermined amount of hydantoin compound; as a powder or granules; as a solution or a suspension in an aqueous liquid or a non-aqueous liquid; as an oil-in-water emulsion; or as a water-in-oil liquid emulsion. Such formulations may be prepared by any of the methods of pharmacy but all methods include the step of bringing into association the hydantoin compound with the carrier which constitutes one or more accessory ingredients. In general they are prepared by uniformly and intimately admixing the hydantoin compound with liquid or finely divided solid carrier(s) or both, and then, if necessary, shaping the product into the desired presentation. For example a tablet may be prepared by compression or moulding a powder or granules of the hydantoin compound, optionally with one or more accessory ingredients. Compressed tablets may be prepared by compressing in a suitable machine, the hydantoin compound in a free-flowing form such as a powder or granules optionally mixed with a binder, lubricant, inert diluent, surface active or dispersing agent(s). Moulded tablets may be made by moulding in a suitable machine the powdered hydantoin compound moistened with an inert liquid diluent.

Formulations suitable for buccal (sub-lingual) administration include lozenges comprising a hydantoin compound in a flavoured base, usually sucrose and acacia or tragacanth; and pastilles comprising a hydantoin compound in an inert base such as gelatin and glycerin; or sucrose and acacia.

Formulations suitable for topical application to the skin preferably take the form of an ointment, cream, lotion, paste, gel, spray, aerosol or oil. Carriers which may be used include vasoline, lanoline, a polyethylene glycol, an alcohol and combinations thereof. The active ingredient is generally present in a concentration of from 0.1 to 15% w/w of the composition, for example from about 0.5 to about 2% w/w.

Formulations of the present invention suitable for parenteral administration conveniently comprise sterile aqueous preparations of a hydantoin compound, which preparations are preferably isotonic with the blood of the intended recipient. These preparations are preferably administered intravenously, although administration may also be effected by means of subcutaneous or intramuscular injection. Such preparations may be conveniently prepared by admixing the hydantoin compound with water and rendering the product sterile and isotonic with the blood.

Formulations suitable for rectal administration are preferably presented as unit-dose suppositories. These may be prepared by admixture of the hydantoin compound with one or more of the conventional solid carriers, for example cocoa butter, and shaping of the resulting mixture.

It will be appreciated from the foregoing that what we claim may comprise any novel feature described herein principally but not exclusively:

(a) The novel compounds of formula (I) as hereinbefore defined.

(b) A method for the preparation of the novel compounds of formula (I) as hereinbefore described.

(c) A pharmaceutical formulation comprising a compound of formula (I) in association with a pharmaceutically acceptable carrier therefor and methods for the preparation of such formulations.

(d) A method for lowering blood pressure in a mammal, including man, which comprises administration to the mammal of an effective hypotensive, non-toxic amount of a compound of formula (I).

(e) A method for the treatment or prophylaxis of thrombosis in a mammal, including man, or mammalian, including human, tissue, which comprises administration of a non-toxic, effective anti-thrombotic amount of a compound of formula (I).

(f) A method for inducing vasodilation in a mammal, including man, comprising administration to said mammal of a non-toxic effective vasodilatory amount of a compound of formula (I).

(g) A method for the treatment or prophylaxis of gastric lesions in a mammal including man comprising administration to said mammal of a non-toxic effective prophylactic or therapeutic amount of a compound of formula (I).

(h) A method for inducing bronchodilation in a mammal, including man, comprising administration to said mammal of a non-toxic, effective bronchodilatory amount of a compound of formula (I).

(i) A method for the treatment or prophylaxis of an allergic condition in a mammal, including man, comprising administration to said mammal of a non-toxic effective prophylactic or therapeutic anti-allergic amount of a compound of formula (I).

(j) A method for inducing abortion of a foetus in a mammal, including man, comprising administration to said mammal of a non-toxic effective abortifacient amount of a compound of formula (I).

(k) A method for inducing infertility in a mammal, including man, comprising administration to said mammal of a non-toxic effective contraceptive amount of a compound of formula (I).

(l) A method of treating a proliferative skin disease in a mammal which comprises bringing an effective therapeutic amount into contact with the skin lesion.

(m) A compound of formula (II), (III), (IV), (VI), (VII), (VIII) or (X) as defined hereinabove, where novel.

EXAMPLE 1

Diethyl 2-aminononanedioate (5.0 g) was heated with benzaldehyde (2.15 g) in benzene (10 ml) under reflux for 1⅔ hr, removing the water formed by means of a Dean and Stark apparatus. The benzene was evaporated in vacuo and the residual oil was taken up in dry tetrahydrofuran (20 ml), stirred under dry nitrogen, treated with sodium hydride (0.61 g of a 80% dispersion in mineral oil), and heated until evolution of hydrogen began. Thereafter reaction was allowed to procede at room temperature. When effervescence had ceased, the pale yellow-brown solution was cooled in ice-water and, with continued stirring, treated with methyl iodide (6.83 g); the cooling bath was removed after 15 min and the mixture was set aside at room temperature overnight. The resulting suspension of solid was diluted with ether (100 ml) and shaken with ice-cold water (100 ml), and the ethereal phase was washed with $H_2O$, dried over sodium sulphate, and evaporated, to leave crude diethyl 2-(benzylideneamino)-2-methylnonanedioate (6.4 g) as a yellow oil.

The above Schiff base (4.3 g) was stirred with 1 N hydrochloric acid (21.5 ml) at room temperature for 30 min and the mixture was then shaken with 0.1 N hydrochloric acid (43 ml) and toluene (20 ml). The aqueous phase was separated, washed with toluene (20 ml), stirred with ether (40 ml), and cautiously basified with aqueous sodium carbonate; the ethereal phase was separated, washed with $H_2O$, dried over magnesium sulphate, and evaporated, to give diethyl 2-amino-2-methylnonanedioate (2.27 g) as an almost colourless oil, $\delta$4.15 and 4.09 (4H, overlapping quartets, ester $CH_2$ groups), 2.68 (2H, broad singlet, exch, $NH_2$), 2.28(2H, triplet, $CH_2$ adjacent to $CO_2Et$) and 1.35 (3H singlet, isolated $CH_3$) in $CDCl_3$.

EXAMPLE 2

A mixture of diethyl 2-amino-2-methylnonedioate (2.73 g) with oct-1-en-3-one (1.323 g) was set aside at room temperature overnight. The resulting diethyl 2-methyl-2-[(3-oxooctyl)amino] nonanedioate was taken up in ethanol (40 ml), treated with sodium borohydride (0.38 g) and stirred at room temperature for 2½ hours. The ethanol was evaporated in vacuo, the residue was shaken with water and ether, and the ethereal solution was washed with water and dried over magnesium sulphate. Removal of the ether left diethyl 2-[(3-hydroxyoctyl)amino]-2-methylnonanedioate as an oil (4.14 g) which was taken up in ethanol (20 ml) cooled in ice-water, and treated with 2 N hydrochloric acid (10 ml) followed by potassium cyanate (1.62 g) in water (5.5 ml). The cooling bath was removed and the mixture was stirred overnight at room temperature; the ethanol was evaporated in vacuo, water (75 ml) was added, and the resulting gum was extracted into ether (75 ml). The ethereal solution was washed with water, dried over magnesium sulphate, and evaporated, and the residual oil was heated on the steam-bath for 6 hr, to give crude 5-(6-ethoxycarbonylhexyl)-1-(3-hydroxyoctyl)-5-methylhydantoin as a yellow brown oil. The latter was stirred in water (20 ml) with 2 N aqueous sodium hydroxide (10 ml) for 2 hr, residual oil was removed with ether, and the aqueous solution was acidified to Congo Red with hydrochloric acid. The liberated carboxylic acid was taken into ether and the ethereal solution was washed with water and dried over magnesium sulphate; removal of the ether left an oil (2.44 g) which was purified by chromatography on silica in 30:1 chloroform-methanol yielding 5-(6-carboxyhexyl)-1-(3-hydroxyoctyl)-5-methylhydantoin as a mixture of diastereomers. Separation by means of high performance liquid chromatography (20–44μ Biosil, chloroform-methanol-acetic acid 97:1.5:1.5) afforded the individual racemic diastereomers as colourless gums, the less polar isomer having $r_f$ 0.47 relative to $r_f$ 0.43 for the more polar isomer on $SiO_2$ in chloroform-methanol-acetic acid 90:5:5. The less polar isomer gave characteristic 'H n.m.r. signals at δ9.30 (1H, broad singlet, exch., NH), 6.22 (2H, broad singlet, exch.,$CO_2H$ and OH), 3.6 (2H, multiplet, C-15 methine and one C-13 proton), 3.0 (1H, multiplet, one C-13 proton), 2.31 (2H,triplet, $CH_2$ adjacent to $CO_2H$), 1.40 (singlet, isolated $CH_3$ and 0.87 (3H, triplet, terminal $CH_3$) in $CDCl_3$. The more polar isomer gave characteristic 'H n.m.r signals at δ9.08 (1H, broad singlet, exch.,NH), 5.41 (2H, broad singlet exch., $CO_2H$ and OH), 3.6 (1H, multiplet, C-15 methine), 3.3 (2H, multiplet, C-13 protons), 2.32 (2H, triplet, $CH_2$ adjacent to $CO_2H$), 1.41 (singlet, isolated $CH_3$) and 0.88 (3H, triplet, terminal $CH_3$) in $CDCl_3$.

EXAMPLE 3

By sequential reaction of diethyl 2-amino-2-methyl-nonanedioate with cyclohexyl vinyl ketone, sodium borohydride, and cyanic acid according to the general procedure described in Example 2,5-(6-carboxyhexyl)-1-(3-cyclohexyl-3-hydroxypropyl)-5-methylhydantoin was obtained as a mixture of diastereomers. Separation by high performance liquid chromatography give the individual racemic diastereomers as colourless gums, the less polar isomer having $r_f$ 0.52 relative to $r_f$ 0.48 for the more polar isomer on $SiO_2$ in chloroform-methanol-acetic acid 90:5:5. The less polar isomer gave characteristic 'H n.m.r. signals at δ9.34 (1H, broad singlet, exch.,NH), 5.83 (2H, broad singlet, exch., $CO_2H$ and OH), 3.6, 3.3 and 3.1 (3H, three multiplets, C-13 protons and C-15 methine), 2.31 (2H, triplet, $CH_2$ adjacent to $CO_2H$) and 1.39 (singlet, isolated $CH_3$) in $CDCl_3$. The more polar isomer gave characteristic 'H n.m.r. signals at δ9.23 (1H broad singlet, exch., NH), 5.73 (2H, broad singlet, exch., $CO_2H$ and OH), 3.38 (3H, multiplet, C-15 methine and C-13 protons), 2.32 (2H, triplet, $CH_2$ adjacent to $CO_2H$) and 1.40 (singlet isolated $CH_3$) in $CDCl_3$.

EXAMPLE 4

Preparation of 5,5-Bis-(6-carboxyhexyl)-1-(3-cyclohexyl-3-hydroxypropyl) hydantoin In the method of Example 1, the methyl iodide was replaced by ethyl 7-bromoheptanoate to give diethyl 2-amino-2-(6-ethoxycarbonylhexyl) nonanedioate.

This compound was then treated by the method of Example 3, but without the separation of diastereomers, to give 5,5-bis-(6-carboxyhexyl)-1-(3-cyclohexyl-3-hydroxypropyl) hydantoin, a colourless crystalline solid, melting point 116°–118° C.

EXAMPLE 5

Interconversion of diastereomers

A solution of the hydantoin diastereomer to be converted is prepared in N-sodium hydroxide solution and allowed to stand at room temperature for several hours. The solution is then acidified and extracted with ether, and the ether extract is washed with water, dried and evaporated.

By means of high performance liquid chromatography the product remaining may be separated into two diastereomers: one identical with the starting material and the other being the other (second) diastereomer.

In similar fashion, the second diastereomer may converted into a mixture of approximately equal quantities of itself with the first diastereomer, and the pure diastereomers isolated by means of high performance liquid chromatography.

EXAMPLE 6

Inhibition of Platelet Aggregation

Aggregation of platelets in 1 ml. of fresh human platelet rich plasma (PRP) was monitored in a Born aggregometer.

The compound to be tested was added to the PRP at the desired concentration, and the resulting mixture incubated at 37° C. for 1 minute after which platelet aggregation was stimulated by the addition of adenosine diphosphate (ADP) to a concentration of 5 μM.

The anti-aggregatory effect of the compound was assessed by measuring the percentage inhibition of platelet aggregation in the presence of the compound as compared with when it was absent. The percentage inhibitions at various concentrations of hydantoin and prostaglandin $E_1$ ($PGE_1$) were established and compared to show activity compared to $PGE_1$.

TABLE 1

| Compound of Example No. | More or less polar diastereomer | Inhibition of Platelet aggregation (X $PGE_1$) |
|---|---|---|
| 2 | less | 0.03 |
|  | more | <0.01 |
| 3 | less | 1.1;2.3 |
|  | more | 0.04 |
| 4 | not relevant | 0.05 |

EXAMPLE 7

Cardiovascular effects in rats

Male normotensive rats Wistar (Charles River) strain, (250–350 g) were anesthetised (chloroform) prior to cannulation of the left femoral vein and anaesthesia maintained by intravenous chloralose (60 mg/kg). Pulsatile blood pressure was recorded from the left femoral artery with an electronic transducer (Bell and Howell Type 4-327 L221) and integrated heart rate was measured with a cardiotachometer triggered from the arterial pressure waves.

The test compound(any one of those used in Example 6) was administered as a solution in physiological saline by intravenous injection via the femoral cannula. The responses recorded were allowed to return to the pre-injection levels between successive administrations.

Injections of the vehicle alone in volumes equivalent to those containing drug did not produce hypotension.

The test compounds; (i.e. each of those in Example 6) showed less than one percent of the hypotensive effect of prostacyclin.

EXAMPLE 8

| Tablet Formulation | In one tablet |
|---|---|
| Compound (less polar diastereomer of Example 3) | 10.0 mg |
| Microcrystalline cellulose B.P. | 200.0 mg |
| Starch B.P. | 15.0 mg |
| Magnesium Stearate | 1.0 mg |

The Compound is dissolved in a volatile solvent. (The compound is soluble in methanol and in ethanol.) The solution is then evenly distributed over the microcrystalline cellulose, and then blended with the starch and then with the magnesium stearate. The mixture is then pressed to tablets, each 226 mg in weight.

EXAMPLE 9

| Capsule Formulation | In one capsule |
| --- | --- |
| Compound as used in Example 8 | 10 mg |
| Polyethylene glycol 4000 | 190 mg |
| Magnesium Stearate | 1 mg |

The polyethylene glycol is melted and the compound is stirred in, and the mixture cooled to room temperature. The wax produced is ground to give granules, which are mixed with the magnesium stearate and then filled into hard gelatine capsules containing 201 mg of mixture.

EXAMPLE 10

| 1 μg/ml Injection | |
| --- | --- |
| Compound (as used in Example 8) | 100 μg |
| Water for Injection | to ...... 100 ml |

Dissolve the Compound in the Water for Injection. Sterilise the solution by filtration through a membrane filter, 0.22 μm pore size, collecting the filtrate in a sterile receiver. Under aseptic conditions, fill the solution into sterile glass ampoules, 1 ml per ampoule; seal by fusion of the glass.

EXAMPLE 11

| 10 μg/ml Injection | |
| --- | --- |
| Compound (as used in Example 8) | 1 mg |
| Ethyl Alcohol | 10 ml |
| Propylene Glycol | 30 ml |
| Water for Injection | to ........ 100 ml |

Dissolve the Compound in the Ethyl Alcohol, add the Propylene glycol and dilute to volume with Water for Injection.

Sterilise the solution by filtration through a membrane filter, 0.22 μm pore size, collecting the filtrate in a sterile vessel. Under aseptic conditions, fill the solution into sterile glass vials, 10 ml per vial. Close with a sterile rubber plug and secure with an aluminium collar.

EXAMPLE 12

| 100 μg Single dose injection (freeze-dried) | |
| --- | --- |
| Compound (as used in Example 8) | 10.0 mg |
| Mannitol | 2.5 g |
| N/10 Sodium Hydroxide Solution | qs to pH 10.0 |
| Water for Injection | to ...... 100.0 ml |

Suspend the Compound in approximately 20 ml Water. Add sufficient Sodium Hydroxide Solution to produce pH 10 and stir to dissolve the Compound. Add and dissolve the Mannitol and dilute to volume with Water for Injection.

Sterilise the solution by passage through a membrane filter, 0.22 μm pore size, and distribute aseptically into sterile vials, 1 ml per vial. Freeze dry the solutions and seal the containers under aseptic conditions with rubber closures. Each vial contains 100 μg of Compound as its freeze-dried sodium salt.

EXAMPLE 13

| Suppository Formulation | |
| --- | --- |
| Compound (as in Example 8) | 3 mg |
| Massa Esterinum C | to ........ 2 g |

Melt the suppository base at about 40° C. Gradually incorporate the Compound and mix until homogeneous. Pour into suitable moulds and allow to set.

Massa Esterinum C is a commercially available suppository base consisting of a mixture of mono-, di- and tri-glycerides of saturated vegetable fatty acids. It is marketed by Henkel International, Dusseldorf.

EXAMPLE 14

| Soft Gelatine Capsule Formulation | | |
| --- | --- | --- |
| Compound (as used in Example 8) | | 10 mg |
| Vehicle | about | 100 mg |

The compound is diluted into a suitable vehicle which will dissolve the compound and is then filled into soft gelatine capsules, each containing about 110 mg of mixture.

What is claimed is:

1. A compound of formula (I):

$$Z-N\underset{\underset{O}{\parallel}}{\overset{\overset{O}{\parallel}}{\diagup\hspace{-0.5em}\diagdown}}\underset{N_{Z^2}}{\overset{Z^3\;Z^1}{\diagup}} \quad (I)$$

wherein Z is selected from hydrogen and alkyl of from 1 to 6 carbon atoms;

one of $Z^1$ and $Z^2$ is a group $-CH_2-X-X^1-X^2$ wherein

X is selected from phenylene, $-C\equiv C-$, cis and trans $-CH=CH-$ and $-CH_2-CQ_2$, in which each Q is independently selected from hydrogen and alkyl or the two Q's together form an alkylene radical of four, five or six carbon atoms;

$X^1$ is selected from a covalent bond and a straight or branched alkylene chain having from 1 to 6 carbon atoms, optionally having one of any methylene groups replaced by oxa ($-O-$) or thia ($-S-$) provided that at least one carbon atom separates such an oxa or thia from a $-C\equiv C-$, $-CH=CH-$ or any $-CO-$ group included in the definition of $X^2$; and $X^2$ is selected from carboxyl, carboxamide, hydroxymethylene and alkoxycarbonyl;

and the other of $Z^1$ and $Z^2$ is a group $-Y-Y^1-Y^2-Y^3$ wherein

Y is $-CR_2-CH_2-$ in which each R is independently selected from hydrogen and methyl;

$Y^1$ is carbonyl, methylene, methylene substituted by hydroxyl or methylene substituted by hydroxyl and alkyl;

$Y^2$ is selected from a covalent bond and straight or branched alkylene having from 1 to 7 carbon atoms, optionally substituted in the carbon adjacent $Y^1$ by one or two groups each of which may be alkyl or a cyclic radical;

$Y^3$ is selected from hydrogen, hydroxy, alkoxy of from 1 to 7 carbon atoms, a cyclic radical, phenyl, benzyl, phenoxy and benzyloxy, wherein each of phenyl, benzyl, phenoxy and benzyloxy may be substituted in benzene ring by one or more groups selected from hydroxy, halogeno, nitro, amino alkylcarbonyl amino, alkenyl, alkoxy, phenyl and alkyl which may itself be substituted by one or more halogeno groups; or $Y^2$ and $Y^3$ together form an alkyl group of from 1 to 7 carbon atoms having at least one hydrogen replaced by fluoro;

or Y is selected from a bond, $-CH_2-$ and $-CH_2.CH_2-$ and $Y^1$, $Y^2$ and $Y^3$ taken together form a cycloalkyl having from 3 to 10 carbon, or bicycloalkyl having from 4 to 10 carbon atoms substituted by a hydroxyl group;

and $Z^3$ is selected from $-CH_2-X-X^1-X^2$ as defined above and alkyl of from 1 to 8 carbon atoms; and pharmaceutically acceptable salts thereof:

the term cyclic radical meaning a monovalent non-heterocyclic radical derived by removal of a ring hydrogen atom from a monocyclic or polycyclic compound (other than benzene) having from 3 to 12 ring carbon atoms, which compound may be saturated or unsaturated and may be further substituted by one or more alkyl groups, and optionally one or more hydrogen atoms of such radicals being replaced by fluoro;

wherein, unless otherwise stated, alkyl moieties are selected from those having from 1 to 6 carbon atoms and alkylene moieties are selected from those having from 2 to 4 carbon atoms.

2. A compound of claim 1 wherein Z is hydrogen; one of $Z^1$ and $Z^2$ is represented by the group $-CH_2-X-X^1-X^2$;

wherein X is selected from cis $-CH=CH-$ and $-CH_2-CH_2-$;

$X^1$ is selected from a covalent bond and a straight or branched alkylene having from 1 to 6 carbon atoms; and $X^2$ is selected from carboxyl and alkoxycarbonyl;

and the other of $Z^1$ and $Z^2$ is represented by the group $-Y-Y^1-Y^2-Y^3$;

wherein Y is $-CH_2-CH_2-$; $Y^1$ is carbonyl, methylene, methylene substituted by hydroxy or methylene substituted by hydroxyl and alkyl; $Y^2$ is selected from straight and branched alkylene having from 1 to 7 carbon atoms optionally substituted on the carbon adjacent $Y^1$ by one or two alkyl groups and $Y^3$ is hydrogen; and salts thereof.

3. A compound of claim 1 wherein in formula (I)
Z is hydrogen
one of $Z^1$ and $Z^2$ is a group $-CH_2-X-X^1-X^2$ wherein
X is selected from $-C\equiv C-$, cis and trans $-CH=CH-$ and $-CH_2-CH_2-$;
$X^1$ is selected from a covalent bond and straight and branched alkylene having from 1 to 6 carbon atoms, optionally having one of any methylene groups replaced by oxa ($-O-$) or thia ($-S-$), provided that at least one carbon atom separates such an oxa or thia from a $-C\equiv C-$, $-CH=CH-$ or $-CO-$ group; and
$X^2$ is selected from carboxyl, carboxamide, hydroxymethylene and alkoxycarbonyl;
and the other of $Z^1$ and $Z^2$ is a group $-Y-Y^1-Y^2-Y^3$ wherein
Y, $Y^1$, $Y^2$ and $Y^3$ are as defined in claim 1.

4. A compound of claim 1 wherein
Z is hydrogen,
$Z^3$ is methyl or ω-carboxyhexyl,
$Z^1$ is a group $-CH_2-X-X^1-X^2$ wherein
X is selected from cis and trans $-CH=CH-$ or $-CH_2-CH_2-$,
$X^1$ is $-CH_2.CH_2.CH_2-$, $-CH_2.O.CH_2-$ or $-CH_2.S.CH_2-$; and
$X^2$ is selected from carboxyl and alkoxycarbonyl; and
$Z^2$ is a group $-Y-Y^1-Y^2-Y^3$ wherein
Y is $-CH_2-CH_2-$
$Y^1$ is methylene substituted by hydroxyl or methylene substituted by hydroxyl and alkyl;
$Y^2$ is selected from a covalent bond and straight and branched alkylene having from 1 to 7 carbon atoms optionally substituted in the carbon adjacent $Y^1$ by one or two groups each of which may be alkyl or a cyclic radical as defined in claim 1;
$Y^3$ is hydrogen, alkoxy of from 1 to 7 carbon atoms or a cyclic radical as defined in claim 1.

5. A compound of claim 4 wherein in formula (I) the cyclic radical is cycloalkyl of from 3 to 10 carbon atoms.

6. A compound of claim 5 wherein cycloalkyl is cyclopentyl or cyclohexyl.

7. The diastereomer of a compound claimed in claim 1 which diastereomer is shown to be less polar by thin layer chromatography using silica gel and a solvent system of chloroform:methanol:acetic acid in the proportions of 90:5:5.

8. 5-(6-Carboxyhexyl)-5-methyl-1-(3-cyclohexyl-3-hydroxypropyl)hydantoin.

9. A pharmaceutically acceptable salt of a compound according to claim 8.

10. 5-(6-Carboxyhexyl)-5-methyl-1-(3-cyclohexyl-3-hydroxypropyl)hydantoin, less polar diastereomer.

11. A pharmaceutical composition for medicinal use selected from lowering blood pressure, treatment or prophylaxis of thrombosis, inducing vasodilation, treatment or prophylaxis of a gastric lesion, inducing bronchodilation, treatment of prophylaxis of an allergic condition, inducing abortion of a foetus, inducing infertility and treating a proliferative skin disease comprising an effective amount of a compound of formula (I) as defined in claim 1, or a pharmaceutically acceptable salt thereof, in association with a pharmaceutically acceptable carrier.

12. A composition as claimed in claim 11 wherein the carrier is a liquid.

13. A composition as claimed in claim 11 in the form of a sterile injectable solution.

14. A composition as claimed in claim 13 comprising from 0.001 to 100 ug of a compound of formula (I), or pharmaceutically acceptable salt thereof, per milliliter.

15. A composition as claimed in claim 13 in the form of a unit dose comprising from 0.01 to 1 mg of a compound of formula (I), or pharmaceutically acceptable salt thereof.

16. A composition as claimed in claim 11 wherein the carrier is a solid.

17. A composition as claimed in claim 16 in the form of a unit dose.

18. A composition as claimed in claim 17 in the form of a tablet, capsule, cachet or suppository.

19. A composition as claimed in claim 18 comprising from 0.1 to 50 mg of a compound of formula (I) or pharmaceutically acceptable salt thereof.

20. A composition as claimed in claim 19 comprising 10 mg of a compound of formula (I) or pharmaceutically acceptable salt thereof.

21. A method for lowering blood pressure in a mammal which comprises administration to the mamml of an effective hypotensive, non-toxic amount of a compound of formula (I) as defined in claim 1 or a pharmaceutically acceptable salt thereof.

22. A method for the treatment of prophylaxis of thrombosis in a mammal or mammalian tissue which comprises administration of a non-toxic, effective antithrombotic amount of a compound of formula (I) as defined in claim 1 or a pharmaceutically acceptable salt thereof.

23. A method according to claim 22 wherein the compound is as claimed in claim 8 or a pharmaceutically acceptable salt or alkyl ester thereof.

24. A method according to claim 23 in which the compound is as claimed in claim 10.

25. A method for inducing vasodilation in a mammal comprising administration to said mammal of a non-toxic effective vasodilatory amount of a compound of formula (I) as defined in claim 1 or a pharmaceutically acceptable salt thereof.

26. A method for the treatment or prophylaxis of a gastric lesion in a mammal comprising administration to said mammal of a non-toxic, effective prophylactic or therapeutic amount of a compound of formula (I) as defined in claim 1 or a pharmaceutically acceptable salt thereof.

27. A method fo inducing bronchodilation in a mammal comprising administration to said mammal of a non-toxic, effective bronchodilatory amount of a compound of formula (I) as defined in claim 1 or a pharmaceutically acceptable salt thereof.

28. A method for the treatment or prophylaxis of an allergic condition in a mammal comprising administration to said mammal of a non-toxic effective prophylactic or therapeutic, anti-allergic amount of a compound of formula (I) as defined in claim 1 or a pharmaceutically acceptable salt thereof.

29. A method of inducing abortion of a fetus in a mammal comprising administration to said mammal of a non-toxic effective abortifacient amount of a compound of formula (I) as defined in claim 1 or a pharmaceutically acceptable salt thereof.

30. A method of inducing infertility in a mammal comprising administration to said mammal of a non-toxic effective contraceptive amount of a compound of formula (I) as defined in claim 1 or a pharmaceutically acceptable salt thereof.

31. A method of treating a proliferative skin disease in a mammal which comprises bringing an effective therapeutic amount of a compound of formula (I) as defined in claim 1 or a pharmaceutically acceptable salt thereof into contact with the skin lesion.

* * * * *